United States Patent [19]

Schulte et al.

[11] Patent Number: 4,465,840

[45] Date of Patent: Aug. 14, 1984

[54] PROCESS FOR THE PRODUCTION OF (THIO) HYDANTOINS

[75] Inventors: Bernhard Schulte, Krefeld; Wolfgang Jakob, Moers; Willi Dünwald, Leverkusen; Karl-Heinrich Meyer, Krefeld, all of Fed. Rep. of Germany

[73] Assignee: Bayer Aktiengesellschaft, Leverkusen, Fed. Rep. of Germany

[21] Appl. No.: 438,054

[22] Filed: Nov. 1, 1982

[30] Foreign Application Priority Data

Nov. 11, 1981 [DE] Fed. Rep. of Germany ....... 3144700

[51] Int. Cl.$^3$ .......................................... C07D 233/78
[52] U.S. Cl. ..................................... 548/310; 536/23; 544/60; 544/82; 544/139; 544/296; 544/322; 544/336; 544/357; 544/370; 546/210; 546/256; 546/278; 548/101; 548/110; 548/309; 548/311; 548/313
[58] Field of Search ............... 548/310, 311, 313, 110, 548/101, 309; 546/278, 210, 256; 536/23; 544/370, 139, 60, 82, 322, 357, 336, 296

[56] References Cited

U.S. PATENT DOCUMENTS 4,246,393 1/1981 Zecher et al. ......................... 528/75

FOREIGN PATENT DOCUMENTS 2662 7/1979 European Pat. Off. .
33477 8/1981 European Pat. Off. .

OTHER PUBLICATIONS

Chemical Abstracts, 76: 14401m (1972) [Rapi, G. et al., *J. Chem. Soc.* © 1971, (22), 3827-3829].
Chemical Abstracts 74: 87082c (1971) [Rubba et al., *C. R. Acad. Sci., Ser.* © 1971, 272(5), 475-477].

Primary Examiner—Richard A. Schwartz
Attorney, Agent, or Firm—Connolly and Hutz

[57] ABSTRACT

This invention relates to a process for the production of compounds containing at least one (thio)-hydantoin ring in the molecule by reacting a carbodiimide with hydroxy- or mercapto-succinic acid diesters corresponding to the following general formula:

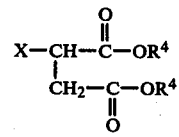

wherein
R$^4$ and X are as defined in the description.

7 Claims, No Drawings

PROCESS FOR THE PRODUCTION OF (THIO) HYDANTOINS

This invention relates to a process for the production of compounds containing at least one (thio) hydantoin ring in the molecule by reaction carbodiimides with hydroxy succinic acid esters or mercapto succinic acid esters.

Hydantoins, polyhydantoins and processes for the production thereof are known (Am. Chem. J. 45, 383; BE-PS No. 678,282).

Low molecular weight hydantoins are preferably used in the pharmaceutical and plant protection fields, while hydantoins of relatively high molecular weight are of significance, for example, for heat-resistant coating compositions (FR-PS No. 1,484,694).

The present invention relates to a new process for the production of compounds containing (thio)hydantoin rings which is characterised in that a carbodiimide is reacted with hydroxy succinic or mercapto succinic acid diesters corresponding to the following general formula:

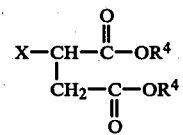

wherein
$R^4$ represents an alkyl, cycloalkyl or benzyl group; and
X represents a hydroxy or mercapto group; at temperatures of from 20° to 250° C., optionally in the presence of a catalyst and optionally in the presence of a solvent.

It is known that, providing suitable catalysts are used, carbodiimides react with alcohols to form O,N,N'-trisubstituted isoureas (cf. for example Chem. Rev., 67, 2 (1967), page 107; Ann. 597, 235 (1955); Chem. Abstr., 54, 5471 (1960)) and with thioalcohols to form the S-substituted isothioureas (cf. Ann., 661, 164 (1963)). In addition, it is known from Ann., 639, 24 (1961) that the reaction of aliphatic carbodiimides with α-hydroxy carboxylic acid esters, for example with the methyl and ethyl esters of glycolic, lactic and α-hydroxy isobutyric acid, leads to the 2-alkyl-imino-3,5-dialkyl-4-oxazolidones. Hydantoins are not obtained in these reactions.

(Thio)hydantoins may be formed by reacting carbodiimides with certain α-hydroxy carboxylic acid esters, such as hydroxy succinic acid diesters (malic acid esters) or sulphhydryl succinic acid diesters, under the conditions according to the present invention in the presence of catalysts which accelerate the addition of OH-functional compounds onto the carbodiimide group.

Using the process according to the present invention, it is possible with particular advantage to synthesise polyhydantoins in non-phenolic solvents, polymers having very high softening temperatures being obtained. The polymers thus obtained are suitable for use as high-temperature-resistant coating compositions, particularly in the field of electrical insulation lacquers, or may even be specifically used for increasing the softening temperatures and for improving the levelling properties of other known insulating compositions.

According to the present invention, monocarbodiimides containing one —N=C=N—group in the molecule, the cyclic dimers or trimers thereof or even linear or branched polycarbodiimides containing more than two carbodiimide groups in the molecule may be used as the carbodiimide compounds.

It is preferred to use carbodiimides corresponding to the following general formualae (I) and (II):

wherein
$R^1$ and $R^2$, which may be the same or different, represent an aliphatic radical containing from 1 to 20 carbon atoms, a cycloaliphatic radical containing from 5 to 12 carbon atoms, an aliphatic-aromatic radical containing from 6 to 20 carbon atoms, an aromatic raical containing from 6 to 16 carbon atoms, an aromatic or cycloaliphatic radical containing from 5 to 12 carbon atoms and containing one or more heteroatoms such as N, O or S, which in either case may optionally be substituted by halogen (chlorine, bromine, iodine or fluorine), nitrile, $C_2$–$C_{12}$ dialkylamino-, $C_7$–$C_{12}$ alkyl arylamino-, $C_2$–$C_{18}$ alkoxy-carbonyl-, $C_7$–$C_{18}$ aroxy-carbonyl-, $C_2$–$C_{18}$ alkyl-carboxy-, $C_7$–$C_{18}$ arylcarboxy-, $C_1$–$C_{18}$ alkoxy-, $C_6$–$C_{18}$ aroxy-, $C_1$–$C_{18}$ alkyl- or halo-alkyl- or nitro groups, or a $C_2$–$C_{12}$ dialkylamino-, $C_2$–$C_{10}$ alkoxy-carbonyl-, $C_6$–$C_{18}$ glycosyl radical or an —Si($R^3$)$_3$—, Sn($R^3$)$_3$— or —SO$_2R^3$— group (wherein $R^3$ $C_6$–$C_{12}$ aryl or $C_1$–$C_8$ arkyl), or which may be attached to one another as members of corresponding cyclic organic radicals; and Y has the same definition as $R^1$ and $R^2$ and preferably represents aliphatic radicals containing from 2 to 12 carbon atoms, cycloaliphatic radicals containing from 5 to 12 carbon atoms, $C_6$–$C_{16}$-aryl radicals or diphenyl radicals attached through O, S, SO$_2$, CH$_2$, CH$_3$—C—CH$_3$, CO, —Si($R^3$)$_2$— or —Sn($R^3$)$_2$— groups; and n represents an integer of from 2 to 2000, preferably from 2 to 1000.

According to the present invention, the monocarbodiimides used are N,N'-symmetrically- and/or asymmetrically-substituted aliphatic, aliphatic-aromatic, cyclic, heterocyclic, aromatic compounds optionally substituted with one or more heteroatoms and containing an —N=C=N—group in the molecule, for example dialkyl carbodiimides, such as dimethyl-, diethyl-, diisopropyl-, dihexyl-, dibutyl-, methyl-t-butyl, dinonyl-, didodecyl-and distearyl-carbodiimide, preferably aromatic, optionally substituted monocarbodiimides, such as diphenyl-ditolyl-, dinaphthyl-carbodiimide, di-p-iodophenyl, di-p-bromophenyl-, di-p-dimethylaminophenyl-, dipyridyl-carbodiimide, dinitro-, -alkoxy-, -aroxy-, -chloro-, -dichloro-, -trichloro-, -tetrachloro-, -pentachlorophenyl-, -benzyl- carbodiimide or carbodiimide dibenzoic acid esters, -diphthalic acid esters, -diisophthalic acid esters, carbodiimide dibenzonitrile, cycloaliphatic carbodiimides, such as dicyclohexyl carbodiimide, and unsaturated carbodiimides, such as diallyl-, dioleyl-and dicycohexenyl-carbodiimide.

These carbodiimide compounds may be obtained by known methods, for example from the corresponding thioureas, in the presence of metal oxides, mercury salts, sodium salts, aryl sulphochlorides, or by the oxidation of thioureas or from S-alkylisothioureas, urea compounds as described, for example, in Chem. Rev., 67, 2

(1967), page 107, or from the corresponding isocyanate compounds with elimination of carbon dioxide in the presence of the known catalysts for the elimination of carbon dioxide (FR-PS No. 1,180,307).

In addition, it is possible to use the N-sulphonyl carbodiimides $RSO_2N=C=NR$, the N-aminocarbodiimides $RN=C=N-NR_2$ or the N,N'-disilyl carbodiimides described, for example, in Chem. Rev., 67, 2 (1967), page 107; Angew. Chem., 77, 430 1965); J. Org. Chem., 29, 2816 (1964); Ann., 652, 21 (1962); Z. Anorg. Allgem. Chem., 330, 101 (1964).

Other starting components suitable for use in accordance with the present invention are aliphatic, cycloaliphatic, araliphatic, aromatic and heterocyclic linear or branched polycarbodiimides containing more than two carbodiimide groups and mixtures thereof or polycarbodiimides which have a statistical composition or a block-like structure comprising different structural elements in a sequence of certain length in the polymer molecule and which may therefore contain the above-mentioned aliphatic, cycloaliphatic, araliphatic, aromatic and heterocyclic structural units in a variety of ratios arranged both in statistical distribution and also blockwise in the polymer molecule.

Where the above-mentioned polycarbodiimides containing two or more carbodiimide groups in the molecule are synthesised from polyfunctional isocyanates, it is possible to use the catalysts known from the literature (cf. for example FR-PS No. 1,180,307), for example phospholines, phospholidine sulphides or even organic metallic compounds of metals of Groups Ia to IIIa of the periodic such as phenyl lithium, diethyl zinc.

The polycarbodiimide compounds according to the present invention may be produced from polyisocyanates of the type comprehensively described, for example, in Annalen 562, pages 75 to 136; Am. Chem. J. 45, 383; DE-OS Nos. 2,908,626 and 2,714,655; EP-PS No. 0,012,379.

It is particularly preferred to use mixtures of polytolylene carbodiimides (2,4- and 2,6-substitution products) or mixtures of poly-p- and m-phenylene carbodiimides and also polycarbodiimides based on aniline/formaldehyde condensates having a polyphenylene-methylene structure and poly-4,4'-diphenyl methane, poly-4,4'-diphenyl ether, poly-p-phenylene, poly-naphthalene carbodiimide, polyisophorone carbodiimide, polyhexamethylene carbodiimide, polycumene carbodiimide, polymesitylene carbodiimide and/or mixtures thereof and also block polycarbodiimides, for example having the following structures:

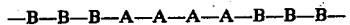

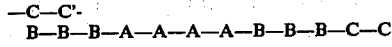

wherein A represents for example, an aromatic structural element, such as diphenyl methane, B represents an aliphatic radical, such as the isophorone radical, and C represents an aromatic unit, such as the tolylene or naphthylene group, which are attached to one another through carbodiimide groups.

These block polycarbodiimides may be produced, for example, by successively subjecting the polyfunctional isocyanates individually used to carbodiimide formation in stages. The indicated structures and commercially readily obtainable bifunctional isocyanates demonstrate the range of variation in regard to the sequence lengths of the quantitative ratios between the individual elements. The polycarbodiimides may even be branched, for example in cases where trifunctional and higher isocyanates are used in the carbodiimide-forming reactions.

α-hydroxy and α-sulphhydryl carboxylic acid ester compounds suitable for use in accordance with the present invention are succinic acid ester derivatives corresponding to the following general formula (III):

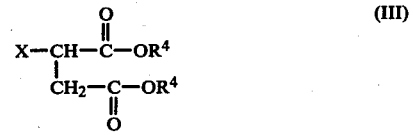

wherein
X represents the —OH— or —SH— group; and
$R^4$ represents an alkyl group containing from 1 to 18 carbon atoms, preferably a methyl, ethyl, propyl, isopropyl or n-butyl radical, or a $C_5$-$C_{12}$ cycloaliphatic radical, preferably a cyclohexyl group or a benzyl radical.

It is particularly preferred to use the methyl, ethyl, cyclohexyl and benzyl diesters of hydroxy succinic acid. The esters suitable for use in the process according to the present invention may be produced, for example, by esterifying malic acid with the corresponding alcohols.

The process according to the present invention may be illustrated, for example, by the following equation:

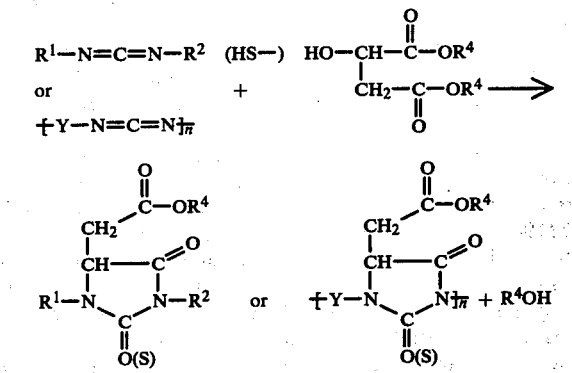

In general, at least one equivalent of hydroxy or sulphhydryl succinic acid ester is used per equivalent of carbodiimide. However, considerable deviations from these stoichiometric quantitative ratios are also possible.

In the event of deviation from the stoichiometric quantitative ratios, other coating compositions may be modified by the process according to the present invention.

The hydantoins according to the present invention may be identified by NMR spectra or by the IR-absorption bands characteristic of hydantoins at 1770, 1710 and 1400–1410 $cm^{-1}$. The polymeric reaction products generally have solution viscosities of from 200 to 200,000 mPas, preferably from 1000 to 100,000 mPas, as measured at 25° C. on 30%, by weight, solutions, for example in phenol, cresol, γ-butyrolactone, N-methyl pyrrolidone, acetophenone, benzoic acid alkyl esters, benzyl alcohol and mixtures thereof.

The reaction according to the present invention may be carried out in phenolic and non-phenolic reaction media which are inert under the reaction conditions or which optionally form loose further-reacting addition compounds or as a heterogeneous reaction in suspension, i.e. in the presence of inert diluents or in the absence thereof or in an excess of one of the reaction components.

Suitable non-phenolic reaction media are diluents, for example inert organic liquids, such as aliphatic, aromatic hydrocarbons, halogenated hydrocarbons, heterocyclic compounds, esters, lactones, ketones, sulphoxides, sulphones, ethers, substituted amides, nitriles, phosphoric acid amides. Examples thereof are cyclohexane, ligroins, carbon tetrachloride, chloroform, methylene chloride, ethylene chloride, tetrachloroethane, methyl ethyl ketone, diisopropyl ether, ethylene glycol or diethylene glycol dimethyl or diethyl ether, dioxane, tetrahydrofuran, toluene, xylenes, chlorobenzene, dichlorobenzene, acetophenone, cyclohexanone, propylene carbonate, caprolactam, caprolactone, butyrolactone, glycol monomethyl ether acetate, dimethyl sulphoxide, tetramethyl sulphone, benzoic acid alkyl esters, N-methyl pyrrolidone, dimethyl formamide, dimethyl acetamide, hexamethyl phosphoric acid triamide, benzonitrile and mixtures thereof.

In addition to these reaction media, it is also possible to use phenolic reaction media, such as phenols, cresols, xylenols, mixtures thereof with the above-mentioned reaction media being particularly suitable. The phenolic solvents are used in such a way that a reaction with the carbodiimide is avoided, i.e. in the reaction with hydroxy or sulphhydryl succinic acid esters catalysed by copper salts, they are advantageously added after reaction of the carbodiimide.

Combinations of low-boiling and relatively high-boiling reaction media, for example mixtures of methylene chloride/chlorobenzene or o-dichlorobenzene or methylene chloride/xylene or toluene or phenol or γ-butyrolactone are preferably used for the production of monohydantoins.

For synthesising the polymeric reaction products, it is particularly preferred to use ternary mixtures of the above-mentioned solvents or diluents, such as methylene chloride/toluene or xylene/γ-butyrolactone or N-methyl pyrrolidone or phenol or cresol. The most readily volatile component is suitable for the dissipation of heat by distillation or as an effective solvent for the polycarbodiimides. The relatively high boiling compound, for example toluene, xylene, "Solvesso", may remain partly or completely in the reaction mixture on completion of the reaction to form the polyhydantoin. These components are preferably diluents commonly used in the field of electrical insulation lacquers. The high-boiling components, such as butyrolactone, N-methyl pyrrolidone, dimethyl formamide, cresol, phenol or mixtures thereof, represent the actual solvents for the reaction product.

Other suitable diluents are cyclohexane, solvent naphtha or, after the reaction of the carbodiimide with the hydroxy succinic or sulphhydryl succinic acid esters, even hydroxy alkyl ethers or aliphatic, aliphatic-aromatic alcohols, such as butanol, aminoalcohols, benzyl alcohol, phenoxy ethanol, the methyl, ethyl, isopropyl and butyl monoethers of ethylene, diethylene or propylene glycol, which enable non-phenolic polymer solutions to be produced.

In cases where carbodiimides are reacted under catalytic conditions with the succinic acid diester derivatives according to the present invention, the alcoholic diluents are added when no more carbodiimide may be detected by IR-spectroscopy.

In cases where non-phenolic inert reaction media are used, the reaction of the carbodiimides with the hydroxy succinic or mercapto succinic acid diesters in accordance with the present invention is preferably carried out in the presence of catalysts which accelerate the addition of OH-functional compounds onto the carbodiimide group. Copper-I-chloride and copper-II-chloride are preferably used.

The further reaction by which the hydantoin is formed may be carried out in the presence of catalysts suitable for rearrangement reactions, such as iodine, acids, such as p-toluene sulphonic acid or acetic acid, and the catalysts accepted as suitable for cyclisation reactions, such as tertiary amines, for example triethylamine, N-methyl morpholine, endoethylene piperazine, metal compounds, such as titanium tetrabutylate, titanium amino alcohol, iron acetylacetonate, dibutyl tin dilaurate, lead acetate, lead naphthenate, lead ethyl hexoate, tin octoate or calcium naphthenate. Other suitable catalysts are nitrogen-containing bases, such as tetraalkyl ammonium hydroxides; alkali metal hydroxides, such as sodium hydroxide; alkali metal phenolates, such as sodium phenolate, or alkali metal alcoholates, such as sodium methylate.

If the reaction of carbodiimides with the hydroxy succinic or mercapto succinic acid diesters in accordance with the present invention is carried out in phenolic reaction media, for example in cresol, the hydantoins may be obtained directly, i.e. without the use of catalysts, for example without the use of copper salt catalysts.

Where carbodiimides obtained in known manner from isocyanates (cf. for example DE-AS No. 1,122,057; US-PS No. 2,941,983) are used, it is possible directly to use this reaction mixture, including the catalyst present therein.

In the practical application of the process according to the present invention, the carbodiimides, preferably dissolved or suspended in a reaction medium, together with the hydroxy succinic or sulphhydryl succinic acid diesters are preferably maintained for from a few minutes to several hours at temperatures of from 20° to 250° C., preferably from 30° to 200° C., in the presence of copper-I-chloride or copper-II-chloride.

The progress of the reaction may be followed, for example, by IR-spectroscopy.

The reaction components are preferably mixed at temperatures of from 20° to 150° C., more preferably from 30° to 100° C., optionally with external cooling, by adding one of the reaction components to the other reaction component introduced beforehand.

In this case, it is possible initially to introduce both the carbodiimides in the form of solutions or suspensions and also the hydroxy succinic or sulphhydryl succinic acid esters with or without other solvents.

In the production of polyhydantoins on a commercial scale, it is advantageous initially to introduce the carbodiimides in the formation of carbodiimides from polyfunctional isocyanates because, after they have been produced, the carbodiimides may be immediately further reacted to form the hydantoin according to the present invention.

In cases where the polycarbodiimides used have a block-like structure —B—A—B— (A and B representing sequences of different chain members), a diisocyanate (for example 4,4'-diisocyanato-diphenyl-methane)

is generally subjected to carbodiimide formation in the above-mentioned reaction media, suitable for the production of monohydantoins, of a readily volatile and substantially involatile liquid, such as methylene chloride/toluene, until an almost complete conversion is obtained. Thereafter, the diisocyanate or even, for example, triisocyanate containing the structural unit B (for example naphthyl, isophorone, tolyl) is added, optionally along with more solvent/diluted, and carbodiimide formation continued, in which case monoisocyanates (for example phenyl, tolyl, naphthyl, cyclohexyl, methyl, cyclohexenyl, oleyl isocyanate, isocyanato-benzoic acid esters, -phthalic acid esters, isophthalitc acid esters) may then be advantageously introduced as regulators as formation of the polycarbodiimide continues. Alternatively, OH- or NH-functional compounds may be used for regulating the molecular weight of the polycarbodiimides. Thereafter, the hydroxy succinic or sulphhydryl succinic acid diesters may be added, optionally in solution in the suitable reaction media mentioned above. The reaction to form the hydantoin is advantageously obtained by increasing the reaction temperature in stages.

The reaction is preferably carried out under an inert gas atmosphere, such as nitrogen or argon.

The reaction according to the present invention may be carried out either continuously or in batches either at normal pressure or under excess pressure.

The low molecular weight reaction products may be worked-up by conventional methods, such as crystallisation or dissolution and reprecipitation.

The monomolecular hydantoins obtainable by the process according to the present invention show activity in the pharmaceutical and plant protection fields.

The polyhydantoins according to the present invention are distinguished by the particularly high temperature resistance thereof. For example, in the testing of a copper wire coated with these polyhydantoins in accordance with DIN 46 453, softening temperatures above 400° C. are observed. In addition, the polymeric reaction products show excellent solubility and outstanding levelling properties in the coating of electrical conductors and are suitable for use as adhesives, lacquers, films, powders, fibres and mouldings. The properties thereof may be varied within wide limits by the addition of fillers, pigments and low molecular weight and/or high molecular weight components, for example for the production of lacquers and films.

The known polycondensates modified by the process according to the present invention, such as polyurethanes, polyamide imides, polyesters, polyester imides, polyester amide imides, polyhydantoins, polycarbonates, polyamides which are mixed in or precondensed and/or co-condensed optionally using, for example, polycarboxylic acids, their anhydrides, esters, polyols, in the production of the polyhydantoins in accordance with the present invention, (modification reactions of this type are known, for example, from DE-OS Nos. 2,908,626 and 2,714,655) show improved temperature behaviour and considerably improved levelling properties in cases where products modified in this way are used for coating heat-resistant substrates.

Where they are produced in cresol-free solvents, the hydantoins according to the present invention are particularly suitable for the modification of polyesters containing tris-hydroxy ethylene isocyanurate soluble in cresol-free solvents, the known critical levelling properties of these polyesters and also the softening temperatures thereof being significantly improved and non-phenolic lacquer solutions characterised by excellent wire-lacquering properties being obtained.

The quantities in which these additives are used may vary considerably according to the application envisaged. Quantities of from 5 to 500%, by weight, are preferably used, based on the polyhydantoins according to the present invention.

The polyhydantoins according to the present invention are preferably used for stoving lacquers, particularly wire lacquers and electrical insulating lacquers, the solids content of the possible lacquer solutions or lacquer mixtures being variable within wide limits and being determined both by the solvent behaviour of the binders and also by the particular application envisaged. The solids content is preferably from 20 to 75%, by weight. The polyhydantoins may be processed both in the form of solutions using conventional lacquering machines and also in the form of impregnating lacquers for solids contents of up to 60%, optionally even in melt form or powder form.

EXAMPLES

EXAMPLE 1

49.7 g of a 19.5%, by weight, diphenyl carbodiimide solution (0.05 mole) in γ-butyrolactone having the typical IR-absorption bands at 2110/2140 cm$^{-1}$ are initially introduced.

8.1 g (0.05 mole) of malic acid dimethyl ester (hydroxy succinic acid dimethyl ester) are added dropwise over a period of 10 minutes at 60° C. The temperature is then increased to 100° C. over a period of 2 hours. The IR-spectrum shows that the diphenyl carbodiimide has not yet reacted. After cooling to room temperature, 30 mg of copper(I)chloride are added and, after 15 minutes at 60° C., no more carbodiimide may be detected in the IR-spectrum. The temperature is increased to 100° C. over a period of 1 hour and, after the addition of 20 mg of diazabicyclooctane and 10 g of toluene, the reaction mixture is heated to 160° C. over a period of 4 hours, the transition temperature rising to 68° C. After stirring for 2 hours at 180° C., analysis of the distillate by gas chromatography reveals methanol in a quantity of 1.2 g (based on the percentage areas). After filtration of the reaction solution, the reaction product is precipitated from 300 ml of water. Drying in vacuo leaves 11.6 g of a brownish product which shows the typical hydantoin and ester bands in the IR spectrum (1770 cm$^{-1}$, double band at 1730/1715 cm$^{-1}$ and ring band at 1410 cm$^{-1}$). After recrystallisation from methanol, the following proton signals are detected in the NMR spectrum (CDCl$_3$):

| | |
|---|---|
| ⌬— | Chem. displacement δ = 7.1–7.6 ppm |
| \|<br>—CH | Chem. displacement δ = 4.8–4/95 ppm (triplet) |
| —OCH$_3$ | Chem. displacement δ = 3.6–3.65 ppm (singlet) |
| —CH$_2$—CO— | Chem. displacement δ = 2.9–3.0 ppm (triplet) |

In the indicated sequence of the protons, the integration curves of the NMR show a ratio of 10:1:3:2, thus confirming the structure of the 1,3-diphenyl hydantoyl-5-acetic acid methyl ester.

EXAMPLE 2

41.2 g of polydiphenyl methane carbodiimide (0.2 mole) containing 0.025 mole of terminal phenyl carbodiimide groups in 150 g of chlorobenzene (produced by subjecting 47 g of 4,4'-diisocyanatodiphenyl methane to carbodiimide formation in the presence of 0.5 g of a mixture of 1-methyl-1-phospha-2-cyclopentene-1-oxide and 1-methyl-1-phospha-3-cyclopentene-1-oxide and 3 g (0.025 mole) of phenyl isocyanate for regulating molecular weight, the reaction being carried out with heating in chlorobenzene) are initially introduced at from 70° to 75° C. The viscous, cloudy polycarbodiimide suspension shows the characteristic IR-bands at 2110/2140 $cm^{-1}$.

50 mg of copper-I-chloride are added and a solution of 32.4 g (0.2 mole) of hydroxy succinic acid dimethyl ester in 10 g of chlorobenzene and 40 g of γ-butyrolactone is homogeneously stirred in at from 70° to 75° C.

The reaction temperature is then increased to from 100° to 105° C. by heating for 30 minutes. The polycarbodiimide is completely reacted. Heating to 130° C. over a period of 1 hour produces 5.4 g of distillate up to a transition temperature of approximately 100° C. According to analysis by gas chromatography, 80% of the distillate consists of methanol. The temperature is then increased to 180° C. over a period of 2 hours during which distillation continues and 150 g of m-cresol 70 are added. After another 4 hours at 185° C., a polymer solution having a solids content of 26.8% (stoved for 5 minutes at 360° C.) and a viscosity of 270 mPas (as determined on a 15% solution in m-cresol at 20° C. using a Hoppler viscometer) is obtained. The polymer precipitated from methanol shows the bands typical of hyandtoin structures at 1775, 1720 and 1410 $cm^{-1}$.

In a lacquering test carried out with this polyhydantoin solution on a 0.7 mm diameter copper wire in a vertical lacquering machine (oven length 4 meters), the favourable levelling properties for which polyhydantoins are known are in evidence, while softening temperatures above 400° C. are determined in accordance with DIN 46 453 for wire speeds of from 7 to 10 m/minutes and stoving temperatures of 400° C. For a wire speed of 7 meters per minute, the lacquered wire shows the following properties, for example: softening temperatures above 468° C., heat shock values of from 220° to 260° C., an edge fibre elongation of up to 67%, abrasion resistances (NEMA) of 30 and a dielectric strength of the order of 6 kV.

EXAMPLE 3

16.2 g (0.1 mole) of hydroxy succinic acid dimethyl ester are initially introduced at room temperature in the form of a 40% solution in 52.4 g of m-cresol 70. After the addition of 45.5 g of a 42.7%, by weight, diphenyl methane carbodiimide solution in $CH_2Cl_2$ (0.1 mole), the mixture is stirred for 4 hours at from 30° to 35° C. No reaction of the carbodiimide is detected in the IR spectrum. After stirring for 2 hours at 60° C., the reaction solution becomes clouded. After another 30 minutes at 80° C., unreacted diphenyl carbodiimide is still observed by IR-spectroscopy. The temperature is then increased to 110° C. over a period of approximately 30 minutes, during which the methylene chloride is distilled off, and is maintained at that level for 4 hours. After 3 hours at 110° C., the IR-spectrum no longer shows the carbodiimide bands at 2110/2140 $cm^{-1}$, although it does show a distinct band at 1710 $cm^{-1}$ and a shoulder at 1770 $cm^{-1}$, indicative of the incipient formation of the hydantoin ring.

The temperature is then increased to from 170° to 175° C. and maintained at that level for 4 hours. The distillate obtained contains 84.5% of the theoretical quantity of methanol. After precipitation from a mixture of methanol and water, the reaction product is obtained in the form of a grey-white powder (17.5 g). After recrystallisation from methanol, the NMR-signals agree with the values quoted in Example 1. The uncrystallised product shows IR-bands at 1770/1730/1710 and 1410 $cm^{-1}$ and has a melting point of 144°–147° C.

EXAMPLE 4

22.6 g of polydiphenyl methane carbodiimide containing approximately 0.1 mole of carbodiimide groups and 0.01 mole of terminal phenyl carbodiimide groups (produced by subjecting 25 g (0.1 mole) of 4,4'-diisocyanato-diphenyl methane to carbodiimide formation by heating to from 45° to 50° C. in the presence of 0.3 g of methyl phospholine oxide and 1.2 g of phenyl isocyanate as regulator) are initially introduced in 40 g of methylene and 40 g of toluene.

30 mg of copper-I-chloride and 30 g of N-methyl pyrrolidone are then introduced. The sump temperature is increased with distillation to 70° C., the stirrability of the polymer being observed and more N-methyl pyrrolidone being kept ready for dilution. The solution shows the IR-bands typical of carbodiimide groups at 2100/2150 and the weaker band at 2040 $cm^{-1}$. After the addition of another 20 g of N-methyl pyrrolidone, a solution of 16.2 g (0.1 mole) of hydroxy succinic acid dimethyl ester in 30 g of N-methyl pyrrolidone is added over a period of 10 minutes at approximately 75° C., followed by heating for about 1 hour to 120° C., resulting in the formation of a clear brown-red solution. The reaction temperature is increased to 180° C. over a period of 1.5 hours, a sample of the lacquer solution showing the IR-bands at 1770/1735/1720 $cm^{-1}$ in the form of shoulders at approximately 140° C. The mixture is then stirred for 3 hours at from 180° to 190° C. and the polymer solution obtained shows pronounced hydantoin bands at 1720/1755 and 1440 $cm^{-1}$. The quantity of methanol theoretically expected is confirmed substantially quantitatively in the distillate by means of a gas chromatogram (based on the percentage areas).

This non-phenolic polyhydantoin solution has a solids content of 32.1% (stoved for 5 minutes at 360° C.), stoving on metal plates resulting in the formation of clear, elastic red-brown polymer films. The polyhydantoin solution obtained has a viscosity of 440 mPas at 20° C. after dilution with N-methyl pyrrolidone to a solids content of 15%.

EXAMPLE 5

(A.)

A polycarbodiimide having a block-like arrangement of the structural elements in the form —B—B—B—A—A—B—B—B— of 25 mole percent of poly-2,4-(80%)— and —2,6(20%)— tolylene carbodiimide (A) and 75 mole percent of polydiphenyl methane carbodiimide (B) containing approximately 0.4 mole of carbodiimide groups (produced by subjecting 17.4 g (0.1 mole) of the diisocyanate of A and 75 g (0.3 mole) of the diisocyanate of B to carbodiimide formation in stages by heating in 140 g of methylene chloride and 140 g of toluene in the presence of 0.75 g of methyl phospholine oxide and 3.6 g (approximately 0.03 mole) of phenyl isocyanate as regulator) are initially introduced at about 50° C. in the form of a highly viscous suspension.

100 mg of copper-I-chloride, 100 g of γ-butyrolactone and 100 g of N-methyl pyrrolidone are then introduced. The mixture is then heated with stirring to from 65° to 70° C. 76 g (0.4 mole) of hydroxy succinic acid diethyl ester in 60 g of N-methyl pyrrolidone and 40 g of γ-butyrolactone are then stirred in over a period of 15 minutes at from 60° to 70° C. The reaction temperature is increased to from 175° to 180° C. over a period of 3 hours, during which the lower boiling solvent components continue to distill off, and is maintained at that level for 4 hours, the reaction mixture being diluted with 20 g of butyrolactone and 40 g of benzyl alcohol as its viscosity increases.

A non-phenolic polymer solution is obtained and has a solids content of 27% (stoved for 5 minutes at 360° C.) and a viscosity of 825 mPas as measured at 20° C. after dilution with γ-butyrolactone/benzyl alcohol (1:1) to a solids content of 15%. The polymer precipitated from methanol and then dissolved and reprecipitated shows the pronounced IR-absorption bands characteristic of hydantoins at 1775/1720/1410 cm$^{-1}$. In a wire lacquering test (oven length 4 meters, 0.7 mm diameter copper wire, wire speed from 7 to 9 meters per minute, stoving temperature 400° C.), this polyhydantoin solution diluted with benzyl alcohol to a solids content of 24% shows good levelling properties and softening temperatures above 400° C., as determined in accordance with DIN 46 453, coupled with very good abrasion resistances and dielectric strengths of up to 7 KV.

(B.)

760 g of a commercial non-cresol-free soluble terephthalic acid/glycerol/ethylene glycol polyester (4 moles of terephthalic acid; solids content approximately 82%; OH-number 145; acid number 4.8) are reacted under nitrogen by stirring for a total of 12 hours at from 160° to 200° C. in the presence of 0.5 g of butyl titanate and 0.5 g of lead acetate following the addition of 360 g (1.38 mole) of tris-hydroxy ethylene isocyanurate at approximately 160° C. After the brief application of a vacuum towards the end of the reaction, a resin, brittle at room temperature, is obtained with a solids content of 88% (3 hours at 200° C.), an OH-number of 286 and an acid number of 5–6.

(C.)

204.5 g of this "theic" polyester are dissolved in Carbitol/xylene (6:4) to form a 50% solution and the resulting solution is mixed with 250 g of the cresol-free 24% polyhydantoin solution prepared in accordance with (A.).

The application of this lacquer mixture to a 0.7 mm diameter copper wire using a wire lacquering machine (oven length 4 meters) at stoving temperatures of 400° C. and wire speeds of from 7 to 10 meters per minute reveals considerably better levelling properties by comparison with the pure "theic" polyester, an increase in the heat shock values to 180° C., an increase in the softening temperatures beyond 330° C. and an improvement in the abrasion resistances for edge fibre elongations of up to 88%, dielectric strengths of up to 8 KV and ageing values of up to 7 days at 180° C. (testing being carried out in accordance with DIN 46 453).

EXAMPLE 6

A block polycarbodiimide (in which the polymer units are grouped thus (—B—A—A—A—A—)$_2$) of 80 mole percent of polydiphenyl methane carbodiimide (A) and 20 mole percent of polynaphthylene carbodiimide (B) containing approximately 0.3 mole of carbodiimide groups (produced by subjecting 62.5 g (0.25 mole) of the diisocyanate of A and 15.3 g (0.065 mole) of the diisocyanate of B to carbodiimide formation in stages by heating in 50 g of methylene chloride, 80 g of chlorobenzene and 50 g of N-methyl pyrrolidone in the presence of 0.5 g of methyl phospholine oxide and in the presence of 3.8 g (0.035 mole) of m-cresol 70/50 mg of endoethylene piperazine for limiting molecular weight is initially introduced at from 50° to 55° C. 100 mg of copper-I-chloride are added, and beginning at 60° C., 57 g (0.3 mole) of hydroxy succinic acid ethyl ester in 50 g of N-methyl-pyrrolidone and 80 g of γ-butyrolactone are introduced over a period of 30 minutes during which the temperature is increased to from 100° to 105° C. The stirrability of the highly viscous reaction solution has to be watched and another 50 g of N-methyl pyrrolidone are added for dilution during the increase in temperature. After about 15 minutes at from 100° to 105° C., no more carbodiimide is detected in the IR-spectrum. 40 g of m-cresol 70 are introduced, after which the temperature is increased to 180° C. over a period of 2.5 hours, during which the lower boiling solvent components continue to distill off and another 30 g of m-cresol 70 are added. The reaction mixture is then stirred for 4 hours at approximately 180° C. The quantity of ethanol theoretically expected is detected substantially quantitatively by gas chromatography in the distillate obtained.

The polymer solution has a solids content of 28.5% (5 minutes at 360° C.) and a viscosity of 630 mPas (as measured at 20° C. after dilution with cresol to a solids content of 15%). The polymer precipitated from methanol shows the IR-absorption bands typical of hydantoins at 1775/1720/1400 cm$^{-1}$. Stoving of samples of this lacquer solution at 360° C. on metal plates leads to clear elastic lacquer films.

We claim:

1. A process for the production of (thio)hydantoin compounds of the formula

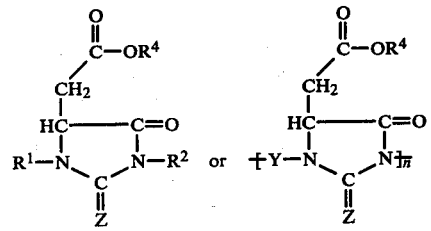

which comprises reacting a carbodiimide of the formula $R^1$—N=C=N—$R^2$ or —Y—N=C=N$_n$ with a diester of the formula

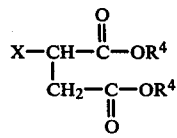

at a temperature from about 20° to about 250° C., wherein $R^1$ and $R^2$ are both the same or are different and each is an aliphatic moiety containing from 1 to 20 carbon atoms, a cycloaliphatic moiety containing from 5 to 12 carbon atoms, an aliphatic-aromatic moiety containing from 6 to 20 carbon atoms, an aromatic moiety containing from 6 to 16 carbon atoms, a $C_2$-$C_{12}$ dialkylamino-, $C_2$-$C_{10}$ alkoxy-carbonyl-, $C_6$-$C_{18}$ glycosyl, —Si($R^3$)-, —Sn($R^3$)$_3$—, —SO$_2R^3$, a heteroaromatic moiety having at least one nitrogen, oxygen or sulfur hetero-atom and from 5 to 12 carbon atoms or a hetero-cycloaliphatic moiety having at least one nitrogen, oxygen or sulfur hetero-atom and containing from 5 to 12 carbon atoms with the hetero-aromatic or hetero-cycloaliphatic being unsubstituted or substituted by at least one substituent selected from halogen, nitrile, $C_2$-$C_{12}$ dialkylamino, $C_7$-$C_{12}$ alkyl arylamino-, $C_2$-$C_{18}$ alkoxy-carbonyl-, $C_7$-$C_{18}$ aroxy-carbonyl-, $C_2$-$C_{18}$ alkyl-carboxy-, $C_7$-$C_{18}$ aryl-carboxy, $C_1$-$C_{18}$ alkoxy-, $C_6$-$C_{18}$ aroxy-, $C_1$-$C_{18}$ alkyl-, $C_1$-$C_{18}$ haloalkyl- and nitro;

$R^3$ is $C_6$-$C_{12}$ aryl or $C_1$-$C_8$ alkyl;

$R^4$ is alkyl having 1 to 18 carbon atoms, $C_5$-$C_{12}$ cycloaliphatic moiety or benzyl;

X is —OH or —SH;

Y is a divalent moiety having the same definition as $R^1$ and $R^2$;

Z is —O— or —S—; and n is an integer from 2 to 2000.

2. The process according to claim 1 wherein the carbodiimide is diphenyl carbodiimide and the diester is malic acid dimethyl ester.

3. The process according to claim 1 wherein the carbodiimide is polydiphenyl methane carbodiimide and the diester is malic acid dimethyl ester.

4. The process according to claim 1 wherein the carbodiimide is a homopolycarbodiimide, a copolycarbodiimide or a block polycarbodiimide of the formula

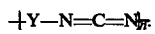

5. The process according to claim 4 wherein the carbodiimide is selected from mixed poly-tolylene-2,4 and 2,6-carbodiimide, mixed phenylene-meta and para-carbodiimide, aniline/formaldehyde condensate, polycarbodiimides comprising polyphenylene methane, poly-4,4'-diphenyl methane carbodiimide, poly-4,4'-diphenyl ether carbodiimide, poly-p-phenylene carbodiimide, poly-naphthalene carbodiimide, polyisophorone carbodiimide, polyhexamethylene carbodiimide, polycumene carbodiimide, polymesitylene carbodiimide and mixtures thereof.

6. The process according to claim 4 wherein the polycarbodiimide is a block polycarbodiimide with the structure comprising

wherein A is tolylene and B is diphenyl methane.

7. The process according to claim 4 wherein the polycarbodiimide is a block polycarbodiimide with the structure comprising 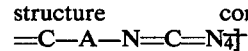 wherein B is naphthylene and A is phenyl methane.

* * * * *